(12) United States Patent
Hornung et al.

(10) Patent No.: US 6,737,125 B2
(45) Date of Patent: May 18, 2004

(54) FLUORINATED CYCLOPENTA[A] NAPHTHALENES AND THEIR USE IN LIQUID-CRYSTAL MIXTURES

(75) Inventors: Barbara Hornung, Hasselroth (DE); Wolfgang Schmidt, Dreieich (DE); Rainer Wingen, Hattersheim (DE)

(73) Assignee: Clariant Finance (BVI) Limited (VG)

( * ) Notice: Subject to any disclaimer, the term of this patent is extended or adjusted under 35 U.S.C. 154(b) by 45 days.

(21) Appl. No.: 10/242,128

(22) Filed: Sep. 12, 2002

(65) Prior Publication Data

US 2003/0108684 A1 Jun. 12, 2003

(30) Foreign Application Priority Data

Sep. 17, 2001 (DE) .......................... 101 45 780

(51) Int. Cl.[7] .................. C09K 19/32; C09K 19/30; C09K 19/34; C07C 25/18; C07D 319/06
(52) U.S. Cl. .............. 428/1.1; 252/299.61; 252/299.62; 252/299.63; 252/299.67; 570/183; 570/187; 549/369
(58) Field of Search .............. 252/299.61, 299.62, 252/299.63, 299.67; 549/369; 570/183, 187; 428/1.1

(56) References Cited

U.S. PATENT DOCUMENTS

| | | | |
|---|---|---|---|
| 4,798,680 A | 1/1989 | Nohira et al. | 252/299.01 |
| 5,384,065 A | 1/1995 | Geelhaar et al. | 252/299.63 |
| 5,550,236 A | 8/1996 | Schlosser et al. | 544/238 |
| 5,744,060 A | 4/1998 | Tarumi et al. | 252/299.63 |
| 5,800,734 A | 9/1998 | Buchecker et al. | 252/299.61 |
| 5,997,766 A | 12/1999 | Kirsch et al. | 252/299.61 |
| 6,083,573 A | 7/2000 | Tarumi et al. | 428/1.1 |
| 6,406,761 B1 | 6/2002 | Tarumi et al. | 428/1.1 |
| 2001/0050352 A1 | 12/2001 | Wingen et al. | 252/299.5 |

FOREIGN PATENT DOCUMENTS

| | | |
|---|---|---|
| DE | 44 27 266 | 2/1995 |
| DE | 195 28 085 | 2/1996 |
| DE | 195 28 665 | 2/1997 |
| DE | 196 29 812 | 2/1997 |
| DE | 195 32 292 | 3/1997 |
| DE | 196 07 996 | 9/1997 |
| DE | 196 54 487 | 7/1998 |
| DE | 198 57 352 | 6/2000 |
| DE | 100 50 071 | 6/2001 |
| DE | 100 26 661 | 11/2001 |
| EP | 0 318 423 | 5/1989 |
| EP | 0 474 062 | 3/1992 |
| EP | 0 665 825 | 8/1995 |
| EP | 0 736 513 | 10/1996 |
| WO | WO 91/08184 | 6/1991 |
| WO | WO 92/11241 | 7/1992 |
| WO | WO 94/26692 | 11/1994 |
| WO | WO 96/00710 | 1/1996 |
| WO | WO 96/30344 | 10/1996 |
| WO | WO 00/04111 | 1/2000 |

OTHER PUBLICATIONS

CAPLUS 2003: 257326, 2003.*
English abstract for EP 0318423, May 31, 1989.
English abstract for WO 91/08184, Jun. 13, 1991.
English abstract for WO 92/11241, Jul. 9, 1992.
English abstract for DE 4427266, Feb. 9, 1995.
English abstract for DE 19528085, Feb. 8, 1996.
English abstract for DE 19607996, Sep. 11, 1997.
English abstract for DE 19857352, Jun. 15, 2000.
English abstract for DE 10050071, Jun. 28, 2001.
English abstract for JP 2001–026561, Jan. 30, 2001.
Ichinose, H., et al., "High optical anisotrophy and small rotational viscosity LC mixture for field–sequential color TN–LCDs", Seventh International Display Workshop, Nov. 25–Dec. 1, 2000, Kobe, Japan, IDW '00, pp. 77–80.
Hird, Michael, et al., "The relationship between molecular structure and mesomorphic properties of 2,2'—and 3,2 –difluoroterphenyls synthesized by palladium–catalysed cross–couplings", Liquid Crystals 1995, vol. 18, No. 1, pp. 1–11.

(List continued on next page.)

*Primary Examiner*—Shean C. Wu
(74) *Attorney, Agent, or Firm*—Alan P. Kass

(57) ABSTRACT

Compounds of the formula (I), liquid-crystal mixtures comprising these compounds, and their use in liquid-crystal displays:

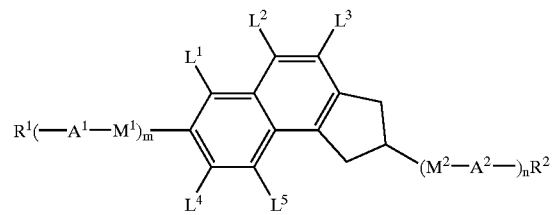

in which

R[1] is H, F, $CF_3$, $OCF_3$, $OCF_2H$, $OCFH_2$, an alkyl radical or alkyloxy radical or an alkenyl radical or alkenyloxy radical;

R[2] is H, an alkyl radical or alkyloxy radical or an alkenyl radical or alkenyloxy radical M[1] is —C(=O)O—, —OC(=O)—, —$CH_2$O—, —O$CH_2$—, —O$CF_2$—, —$CF_2$O—, —C≡C—, —$CH_2CH_2$—, —$CF_2CF_2$—, —CF=CFC(=O)O— or a single bond M[2] is —C(=O)O—, —OC(=O)—, —$CH_2$O—, —O$CH_2$—, —$CH_2CH_2$—, —$CF_2CF_2$— or a single bond;

A[1] and A[2] are α-1,4-diyl, unsubstituted or mono- or disubstituted by F; where α is: phenylene, cyclohexane, 1-cyclohexene or 1,3-dioxane-2,5-diyl;

m and n are zero or 1; m+n=0 or 1

L[1], L[2], L[3], L[4] and L[5] are H or F.

16 Claims, 1 Drawing Sheet

OTHER PUBLICATIONS

Gray, G.W., et al., "The synthesis of serveral lateral difluoro- substituted 4,4"–dialkyl- 4,4"–alkoxyalkyl-terphenyls and a rationalisation of the effect of such substitution on mesophase type and transition temperatures", Mol. Cryst. Liq. Cryst., 1991, vol. 204, pp. 43–64.

Bezborodov, V.S., et al., "The synthesis and properties of some mesomorphic cyclohexene derivatives" Liquid Crystals, 1997, vol. 23, No. 1, pp. 69–75.

Schlosser, Manfred, "Superbase reactions: the expedient and selective metalation of fluorine– or trifluoromethyl–substituted benzenes", Synlett, Dec. 1990, pp. 747–748.

Butera, John, et al., "Computer–assisted design and synthesis of novel aldose reductase inhibitors", J. Med. Chem., 1989, 32, pp. 757–795.

* cited by examiner

FLUORINATED CYCLOPENTA[A] NAPHTHALENES AND THEIR USE IN LIQUID-CRYSTAL MIXTURES

More and more applications of LCDs—for example, use in automobiles, where temperatures across a range from −40° C. to 100° C. may readily occur, and also for portable devices such as cell phones and notebook PCs—are requiring liquid-crystal mixtures combining a very wide range of operating temperatures with a very low threshold voltage.

Consequently there is an ongoing demand for new, appropriate liquid-crystal mixtures and components of such mixtures. As described in Ichinose et al. (IDW,00, Abstr. LCT4-3) or in DE-A-100 50 071, the search is on for materials possessing at the same time both high optical anisotropy (Δn) and low rotational viscosity, along with other parameters such as, for example, high absolute dielectric anisotropy (Δε) values, in addition to further application-relevant parameters.

It is an object of the present invention, therefore, to provide novel components for use in nematic or cholesteric or chiral smectic liquid-crystal mixtures which possess high absolute dielectric anisotropy values in combination with a favorable viscosity/clearing point relationship. Moreover, the compounds should be highly stable to light and UV and also to heat. Furthermore, they should be suitable for realizing high voltage holding ratios (VHRs). In addition, they should be readily available synthetically and thus potentially inexpensive.

DESCRIPTION OF THE DRAWINGS

For the purpose of illustrating the invention, the drawing provides additional information, which helps to define the invention.

Figure 1:
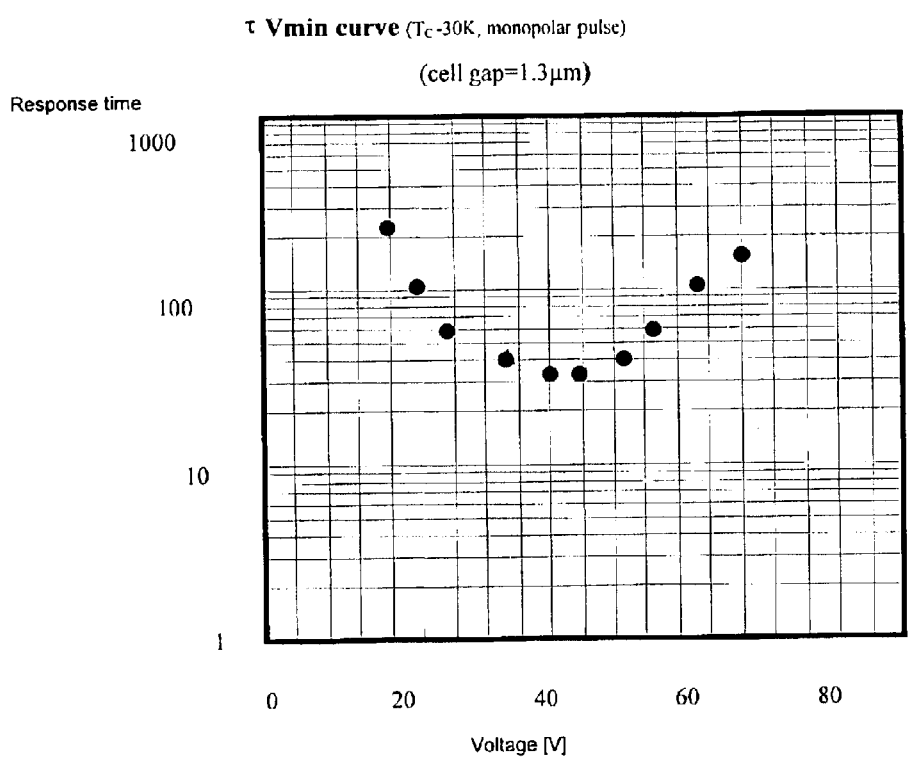
FIG. 1 is a voltage/response time curve, which illustrates the requirement for inverse mode operation.

It has now been found that these requirements are met by the fluorinated cyclopenta[a]naphthalenes of the formula (I)

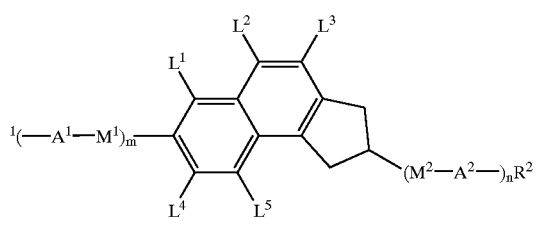
(I)

in which:
$R^1$ is H, F, $CF_3$, $OCF_3$, $OCF_2H$, $OCFH_2$, an alkyl radical or alkyloxy radical having from 1 to 12 carbon atoms or an alkenyl radical or alkenyloxy radical having from 2 to 12 carbon atoms, in which also in each case one (nonterminal) —$CH_2$— group may have been replaced by —O— or —C(=O)O—, one —$CH_2$— group may have been replaced by —C≡C— or cyclopropane-1,2-diyl and/or one or more H may have been replaced by F $R^2$ is H, an alkyl radical or alkyloxy radical having from 1 to 12 carbon atoms or an alkenyl radical or alkenyloxy radical having from 2 to 12 carbon atoms, in which also in each case one (nonterminal) —$CH_2$— group may have been replaced by —O— or —C(=O)O—, one —$CH_2$— group may have been replaced by —C≡C— or cyclopropane-1,2-diyl and/or one or more H may have been replaced by F with the proviso that $R^2$ may not be H if $R^1$ is H, F, $CF_3$, $OCF_3$, $OCF_2H$ or $OCFH_2$ $M^1$ is —C(=O)O—, —OC(=O)—, —$CH_2O$—, —$OCH_2$—, —$OCF_2$—, —$CF_2O$—, —C≡C—, —$CH_2CH_2$—, —$CF_2CF_2$—, —CF=CFC(=O)O— or a single bond $M^2$ is —C(=O)O—, —OC(=O)—, —$CH_2O$—, —$OCH_2$—, —$CH_2CH_2$—, —$CF_2CF_2$— or a single bond $A^1$ and $A^2$ independently of one another are phenylene-1,4-diyl, unsubstituted or mono- or disubstituted by F; cyclohexane-1,4-diyl, unsubstituted or mono- or disubstituted by F; 1-cyclohexene-1,4-diyl, unsubstituted or monosubstituted by F; or 1,3-dioxane-2,5-diyl m and n independently of one another are zero or 1; m+n=0 or 1

$L^1$, $L^2$, $L^3$, $L^4$ and $L^5$ are H or F with the provisos that
a) at least one element from the group $L^1$, $L^2$, $L^3$, $L^4$, $L^5$ is F
b) $L^1$, $L^2$ and $L^3$ are H if $L^5$ is F
c) $L^4$ and $L^5$ are H if $L^3$ is F.

Preference is given to the compounds of the formulae (Ia) to (Ik):

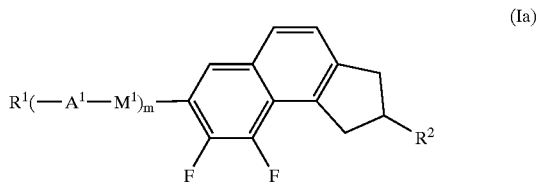
(Ia)

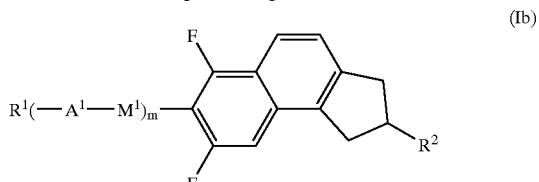
(Ib)

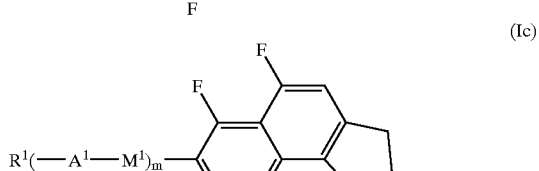
(Ic)

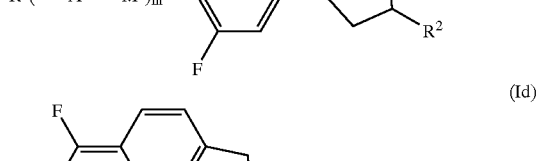
(Id)

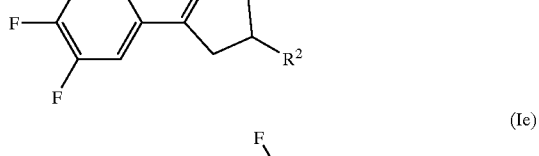
(Ie)

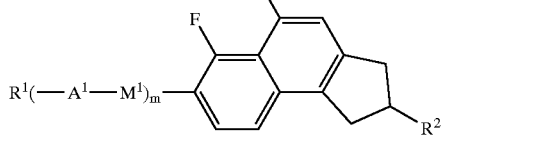

-continued

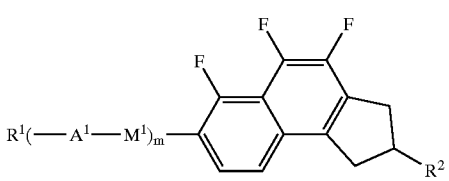
(If)

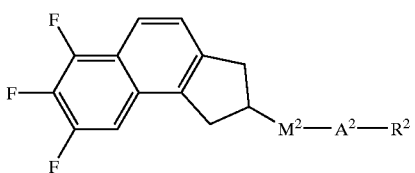
(Ig)

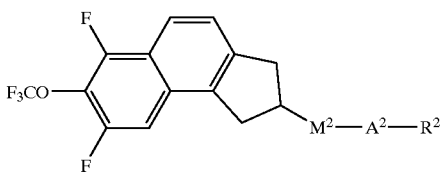
(Ih)

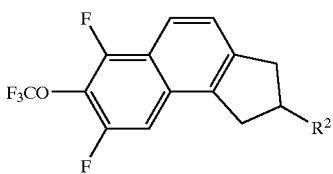
(Ii)

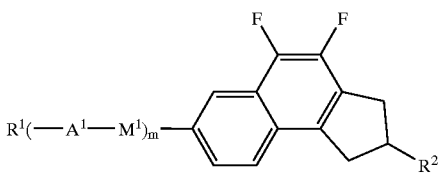
(Ik)

In these formulae, in
(Ia) $R^1$ is H, F, $CF_3$, $OCF_3$, an alkyl radical having from 1 to 12 carbon atoms or an alkenyl radical having from 2 to 8 carbon atoms, in which also in each case one (nonterminal) —$CH_2$— group may have been replaced by —O—
$R^2$ is H or an alkyl radical having from 1 12 carbon atoms
(Ib) $R^1$ is H, F, $CF_3$, $OCF_3$, an alkyl radical having from 1 to 12 carbon atoms or an alkenyl radical having from 2 to 8 carbon atoms, in which also in each case one (nonterminal) —$CH_2$— group may have been replaced by —O—
$R^2$ is H or an alkyl radical having from 1 12 carbon atoms
(Ic) $R^1$ is H, F, $CF_3$, $OCF_3$, an alkyl radical having from 1 to 12 carbon atoms or an alkenyl radical having from 2 to 8 carbon atoms, in which also in each case one (nonterminal) —$CH_2$— group may have been replaced by —O—
$R^2$ is H or an alkyl radical having from 1 to 12 carbon atoms
(Id) $R^2$ is H or an alkyl or alkyloxy radical having from 1 to 12 carbon atoms
(Ie) $R^1$ is H, F, $CF_3$, $OCF_3$, an alkyl radical having from 1 to 12 carbon atoms or an alkenyl radical having from 2 to 8 carbon atoms, in which also in each case one (nonterminal) —$CH_2$— group may have been replaced by —O—
$R^2$ is H or an alkyl radical having from 1 12 carbon atoms
(If) $R^1$ is H, F, $CF_3$, $OCF_3$, an alkyl radical having from 1 to 12 carbon atoms or an alkenyl radical having from 2 to 8 carbon atoms, in which also in each case one (nonterminal) —$CH_2$— group may have been replaced by —O—
$R^2$ is H or an alkyl radical having from 1 to 12 carbon atoms
(Ig) $R^2$ is H, an alkyl radical or alkyloxy radical having from 1 to 12 carbon atoms or an alkenyl radical or alkenyloxy radical having from 2 to 8 carbon atoms, in which also in each case one (nonterminal) —$CH_2$— group may have been replaced by —O— or —C(=O)O— and/or one or more H may have been replaced by F; $M^2$ is a single bond
(Ih) $R^2$ is H, an alkyl radical or alkyloxy radical having from 1 to 12 carbon atoms or an alkenyl radical or alkenyloxy radical having from 2 to 8 carbon atoms, in which also in each case one (nonterminal) —$CH_2$— group may have been replaced by —O— or —C(=O)O— and/or one or more H may have been replaced by F; $M^2$ is a single bond
(Ii) $R^2$ is H or an alkyl radical having from 1 to 12 carbon atoms
(Ik) $R^1$ is H, F, $CF_3$, $OCF_3$, an alkyl radical having from 1 to 12 carbon atoms or an alkenyl radical having from 2 to 8 carbon atoms, in which also in each case one (nonterminal) —$CH_2$— group may have been replaced by —O—
$R^2$ is H or an alkyl radical having from 1 to 12 carbon atoms.

The compounds (Ib), (Id), (Ig), (Ih) and (Ii) are synthesized in accordance with scheme 1.

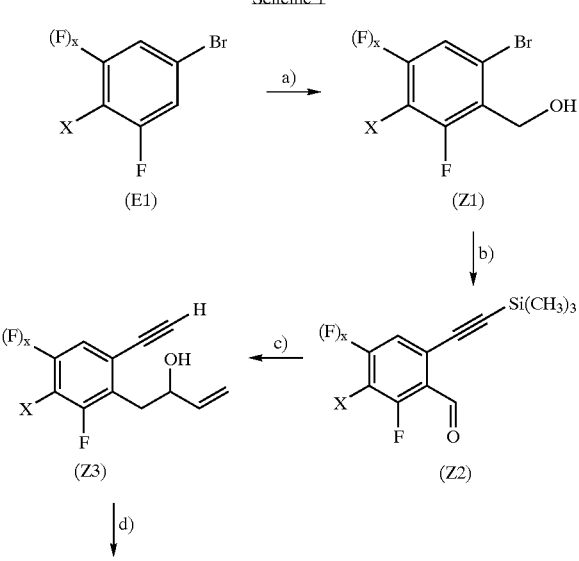
Scheme 1

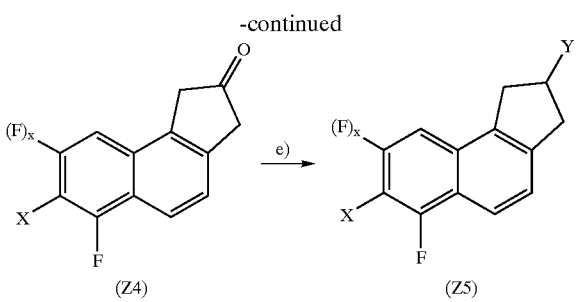

In this scheme 1

X is the radical $R^1-(A^1-M^1)_m-$, in which $M^1$ is not —C(=O)O—, —OC(=O)— or —CF=CFC(=O) O— and if x=1 and m=0 $R^1$ is not H x is 0 or 1

Y is the radical $-(M^2-A^2)_n-R^2$

For compounds (E1) in which X is $R^1$, the following starting materials are known and/or available commercially, for example:

x=0 1-bromo-3,4-difluorobenzene [348-61-8], 4-bromo-2-fluoro-1-(trifluoromethoxy)benzene [105529-58-6], 4-bromo-2-fluoro-1-(difluoromethoxy)benzene [147992-27-6], 4-bromo-2-fluoroanisole [2357-52-0], 4-bromo-1-ethoxy-2-fluorobenzene [115467-08-8], 4-bromo-2-fluoro-1-propoxybenzene, 4-bromo-1-butoxy-2-fluorobenzene [54509-63-6], 4-bromo-2-fluoro-1-pentyloxybenzene [127326-78-7], 4-bromo-2-fluoro-1-octyloxybenzene [119259-26-6], 4-bromo-2-fluoro-1-[(1-methylhexyl)oxy]benzene [129590-26-7], 4-bromo-2-fluoro-1-(2,2,2-trifluoroethoxy)benzene [145767-77-7], 4-bromo-2-fluorotoluene [51436-99-8], 4-bromo-1-butyl-2-fluorobenzene [121386-04-7], 4-bromo-2-fluoro-1-pentylbenzene [134445-80-0]

x=1 1-bromo-3,4,5-trifluorobenzene [138526-69-9], 4-bromo-2,6-difluoro(trifluoromethoxy)benzene [115467-07-7]; 4-bromo-2,6-difluoro(difluoromethoxy)benzene [181806-67-7], 4-bromo-2,6-difluoroanisole [104197-14-0], 4-bromo-2,6-difluoro-1-hexyloxybenzene [130191-95-6], 1-benzyloxy-4-bromo-2,6-difluorobenzene [99045-18-8], 5-bromo-1,3-difluoro-2-(1,1,3,3,3-pentafluoropropoxy)benzene [163155-02-0], 5-bromo-1,3-difluoro-2-methylbenzene [179617-08-4], 5-bromo-2-butyl-1,3-difluorobenzene [160976-00-1]

Compounds (E1) in which X is $R^1-A^1-M^1$ are known from the literature:

x=0 4-bromo-4'-ethyl-2-fluoro-1,1'-biphenyl [116713-40-7], 4-bromo-2-fluoro-4'-propyl-1,1'-biphenyl [116831-33-5], 4'-butyl-4-bromo-2-fluoro-1,1'-biphenyl [116831-34-6], 4-bromo-2-fluoro-4'-pentyl-1,1'-biphenyl [96515-25-2], 4-bromo-4'-hexyl-2-fluoro-1,1'-biphenyl [116831-35-7], 4-bromo-2-fluoro-4'-octyl-1,1'-biphenyl [116831-36-8], 4-bromo-2-fluoro-4'-nonyl-1,1'-biphenyl [116831-37-9], 4-bromo-2-fluoro-1-(trans-4-pentylcyclohexyl)benzene [60975-60-0]

x=1 4-(4-alkylphenyl)- and 4-(4-alkoxyphenyl)-3,5-difluoro-bromobenzenes can be prepared in analogy to WO 91/08184, e.g., by means of a Suzuki reaction between mesogenic boronic acids and 4-bromo-2,6-difluoro-iodobenzene [160976-02-3], 4-bromo-2-fluorophenol [2105-94-4] or 2,6-difluoro-4-bromophenol [104197-13-9] (following conversion to the respective triflate).

By "mesogenic" in this context are meant well-known building blocks of liquid-crystal compounds, typically featuring a para-(alkyl, alkoxy, etc.) substituent on a phenyl ring [which may have further substituents, including rings such as cyclohexane, for example, in an appropriate position (e.g., para)].

For the individual reaction stages it is possible to operate in analogy to the following literature references, hereby incorporated by reference.

a) 1. LITMP 2. HCHO in analogy to DE-1 00 22 661.2
b) 1. $(CH_3)_3SiC≡C-H$, $n-C_4H_9NH_2$, Cu(I)I, $Pd(PPh_3)_2Cl_2$ 2. $MnO_2$ in analogy to Blanco-Urgoiti et al., Tetrahedron Letters 42, 3315 (2001)
c) 1. $Ph_3P=CHOCH_3$ 2. 1N HCl 3. $H_2C=CHMgBr$ 4. $(C_4H_9)_4NF$ in analogy to Blanco-Urgoiti et al., Tetrahedron Letters 42, 3315 (2001)
d) $Co_2(CO)_8$, molecular sieve 4 Å, 110° C. in analogy to Blanco-Urgoiti et al., Tetrahedron Letters 42, 3315 (2001)
e) 1. $BrMg-(A^2)_n-R^2$ 2. $H^+$ 3. $H_2/Pd$ (C)

For compounds of the formula (Ia) the synthesis according to the scheme 2 can be used.

Scheme 2

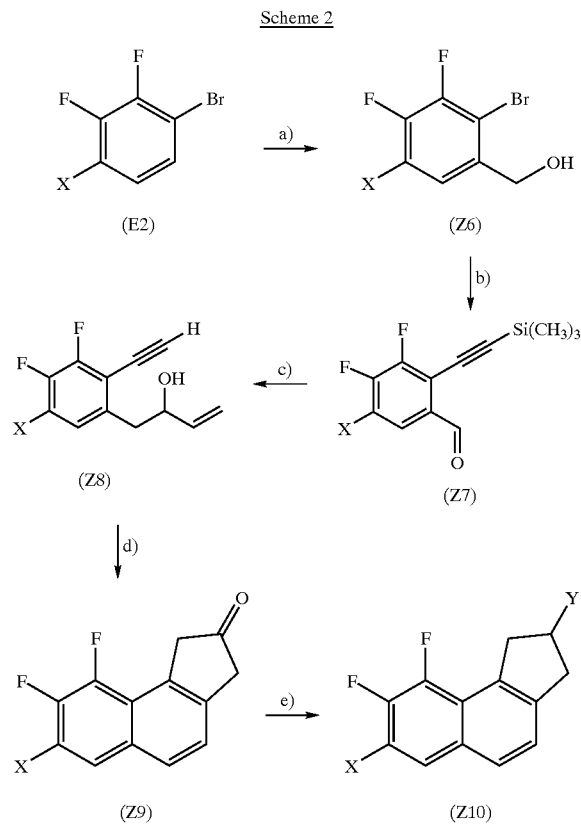

In this scheme 2

X is the radical $R^1-(A^1-M^1)_m-$, in which $M^1$ is not —C(=O)O—, —OC(=O)—or —CF=CFC(=O) O— and if m=0 $R^1$ is not H Y is the radical $-(M^2-A^2)_n-R^2$ The following starting materials (E2) are known from the literature; homologous compounds can be prepared in analogously:

m=0 2,3-difluoro-4-propyl-bromobenzene [181806-74-6], 4-decyl-2,3-difluoro-bromobenzene [223720-87-4], 1-bromo-2,3-difluoro-4-hexyloxybenzene (WO 00/04111), 1-bromo-2,3-difluoro-4-octyloxybenzene (WO 00/04111), 1-bromo-2,3-difluoro-4-(1-methylheptyloxy)-benzene (Liq. Cryst. 1996, 20, 653).

m=1 4-bromo-2,3-difluoro-4'-pentyl-1,1'-biphenyl [151984-58-6], 1-bromo-2,3-difluoro-4-[(trans-4-pentylcyclohexyl)methoxy]-benzene [124728-41-2].

For the individual reaction stages it is possible to proceed in analogy to the following literature references, hereby incorporated by reference.

a) 1. LITMP 2. HCHO in analogy to DE-100 22 661.2
b) 1. $(CH_3)_3SiC\equiv C-H$, $n-C_4H_9NH_2$, Cu(I)I, $Pd(PPh_3)_2Cl_2$ 2. analogy to Blanco-Urgoiti et al., Tetrahedron Letters 42, 3315 (2001)
c) 1. $Ph_3P=CHOCH_3$ 2. 1N HCl 3. $H_2C=CHMgBr$ 4. $(C_4H_9)_4NF$ in analogy to Blanco-Urgoiti et al., Tetrahedron Letters 42, 3315 (2001)
d) $Co_2(CO)_8$, molecular sieve 4 Å, 110° C. in analogy to Blanco-Urgoiti et al., Tetrahedron Letters 42, 3315 (2001)
e) 1. $BrMg-(A^2)_n-R^2$ 2. $H^+$ 3. $H_2$/Pd (C)

For the compounds of the formula (Ie) it is possible to use the synthesis according to scheme 3.

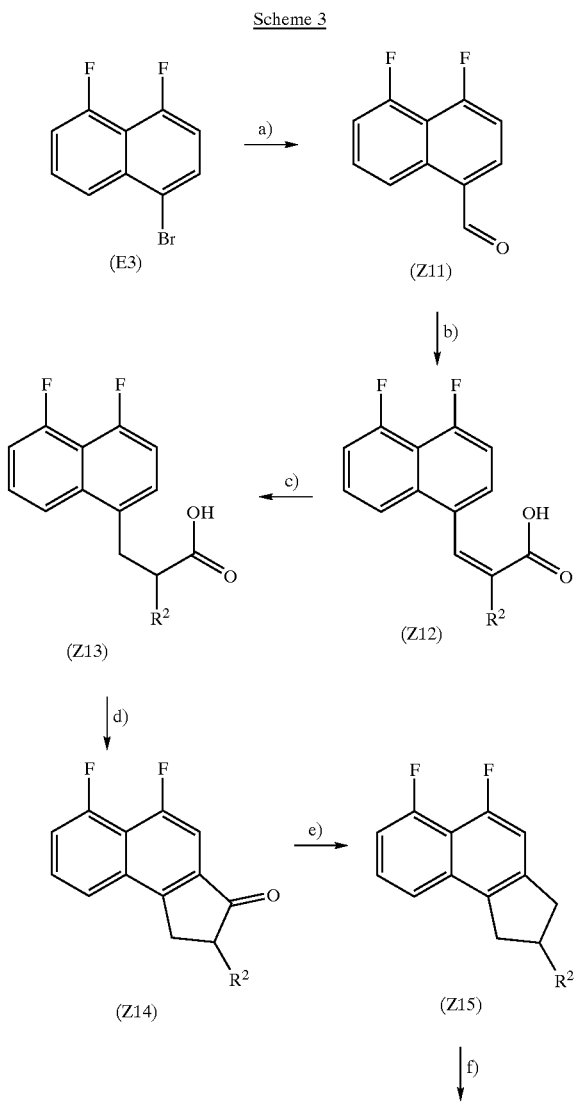

In this scheme 3

X is the radical $R^1-(A^1-M^1)_m-$

The starting material (E3) is known from the literature:

1,8-difluoro-4-bromonaphthalene [52692-38-3]

For the individual reaction stages it is possible to operate in analogy to the following literature references, hereby incorporated by reference.

a) 1. Mg/THF 2. DMF 3. $H_3O^+$ in analogy to DE-100 22 661.2
b) $R_2CH(CO_2H)_2$, piperidine, pyridine in analogy to J.Am.Chem.Soc. 80, 4949 (1958)
c) $H_2$/Pd (C) in analogy to WO94/26693
d) polyphosphoric acid in analogy to J.Med.Chem. 32(4), 757 (1989)
e) $Et_3SiH/F_3CCO_2H$ in analogy to Mol.Cryst.Liq.Cryst. 199,327 (1991)
f) 1. Metalation in analogy to J. Chem. Soc. Perkin Trans. I 1995 2729, Synlett 1990, 747 2. Reaction with an X-electrophile (in analogy to Tetrahedron Lett. 1996, 37, 6551); on this point see also Schemes 5 to 8.

Here and in the schemes below, an X-electrophile is to be understood as referring to a functional derivative, as an electrophile, by way of which the group X can be introduced directly as such; it also refers, however, to a functional derivative which by way of a reaction sequence permits the synthesis of a substituent corresponding to X. Examples of X-electrophiles with which X can be introduced directly as such are alkyl halides (for $X=R^1$ when m=0) or NFSI (for X=F). One example of a reaction sequence for introducing X is the reaction with trimethylborate to give the corresponding boronic acid ($X=B(OH)_2$), the oxidation of that acid to the phenol (X=OH) and the conversion of said phenyl into the trifluoromethoxy compound ($X=OCF_3$) by the method of Hiyama (Bull.Chem.Soc.Jpn.73, 471 (2000)). The phenol (X=OH) may also, for example, be reacted with carboxylic acid or carboxylic acid derivatives to give compounds in which X is $R^1-A^1-C(=O)O-$.

Another example of reaction sequences for introducing X is the reaction of the lithium compound with iodine (X=I) followed by Suzuki reaction with mesogenic boronic acids ($R^1-A^1-B(OH)_2$) to give compounds in which X is $R^1-A^1-$.

For the compounds (If) and (Ik) it is possible to use the synthesis according to scheme 4.

Scheme 4

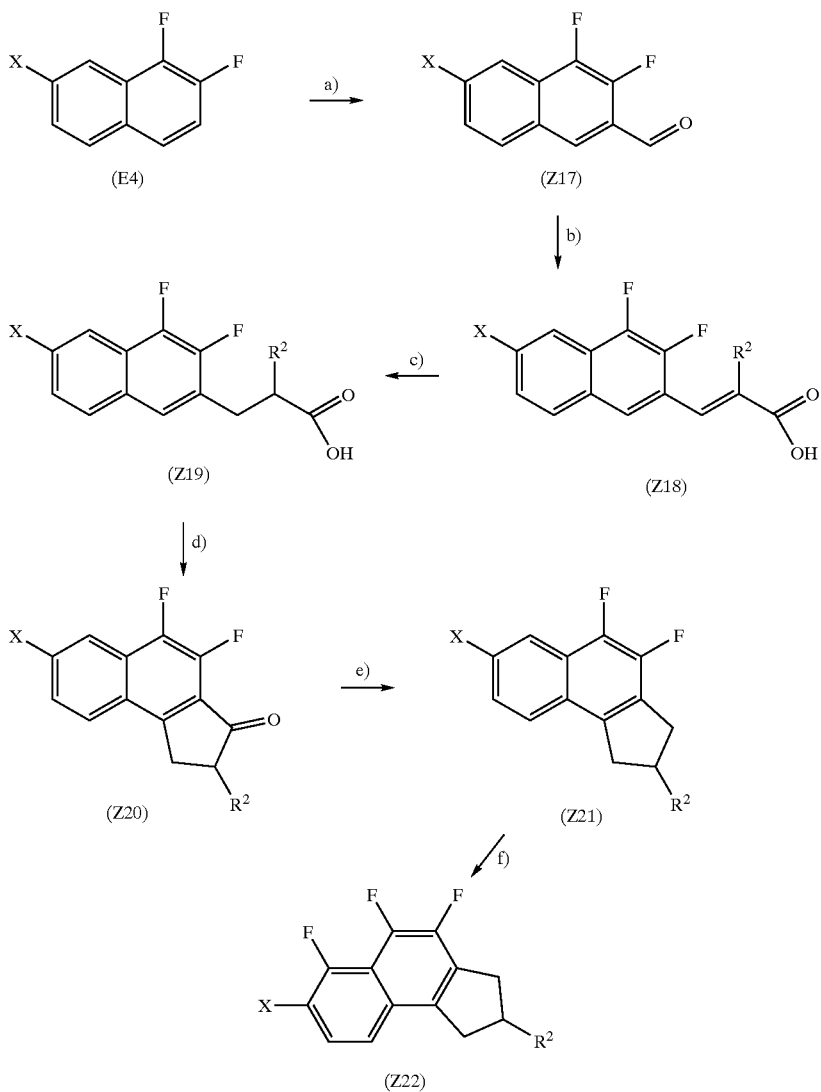

In this scheme 4

X is Cl, Br, I, alkyl, alkanoyl or the radical $R^1$—($A^1$—$M^1$)$_m$, in which $M^1$ is not —C(=O)O—, —OC(=O)— or —CF=CFC(=O)O—

The following starting materials (E4) are known from the literature:

X=H 1,2-difluoronaphthalene [317-80-6] (JP-A 2001026561); X=Cl can be prepared in analogy to (JP-A 2001026561) from 7-chloro-2-naphthol [40492-93-1], X=Br in analogy to (JP-A 2001026561) from 7-bromo-2-naphthol [116230-30-9], X=methyl in analogy to (JP-A 2001026561) from 7-methyl-2-naphthol [26593-50-0], X=propyl in analogy to (JP-A 2001026561) from 7-propionyl-2-naphthol [175226-46-7] following reduction to 7-propyl-2-naphthol.

The compounds where X=Cl or Br may serve in a manner familiar to the skilled worker for the synthesis of the radical $R^1$—($A^1$—$M^1$)$_m$.

For the individual reaction stages it is possible to operate in analogy to the following literature references, hereby incorporated by reference.

a) 1. n-BuLi/KOtBu/THF 2. DMF 3. $H_3O^+$ in analogy to DE-100 22 661.2 b) $R_2CH(CO_2H)_2$, piperidine, pyridine in analogy to J.Am.Chem.Soc. 80, 4949 (1958)

c) $H_2$/Pd (C) in analogy to WO/94/26693 d) polyphosphoric acid in analogy to J.Med.Chem. 32(4), 757 (1989)

e) $Et_3SiH/F_3CCO_2H$ in analogy to Mol.Cryst.Liq.Cryst. 199, 327 (1991)

f) 1. metalation in analogy to J. Chem. Soc. Perkin Trans. I 1995 2729, Synlett 1990, 747 2. NFSI in analogy to Snieckus et al., Tetrahedron Lett. 35, 3465 (1994)

The further reaction of (Z21) to (Ik) and (Z22) to (If)—e.g., Suzuki reactions with mesogenic boronic acids in the case of Y=Cl or Br—is familiar to the skilled worker from the relevant literature (see also Scheme 6).

Generally speaking, cyclopenta[a]naphthalenes obtained in accordance with schemes 1, 3 and 4 and in which X=H may also be reacted by metalation in this position and subsequent reaction with electrophiles (e.g., trimethylborate, DMF, $CO_2$, n-alkyl aldehydes, 4-n-alkylcyclohexanones, iodine, bromine) to give precursors from which the compounds of the formula (I) of the invention can be prepared (schemes 5 to 8).

Scheme 5
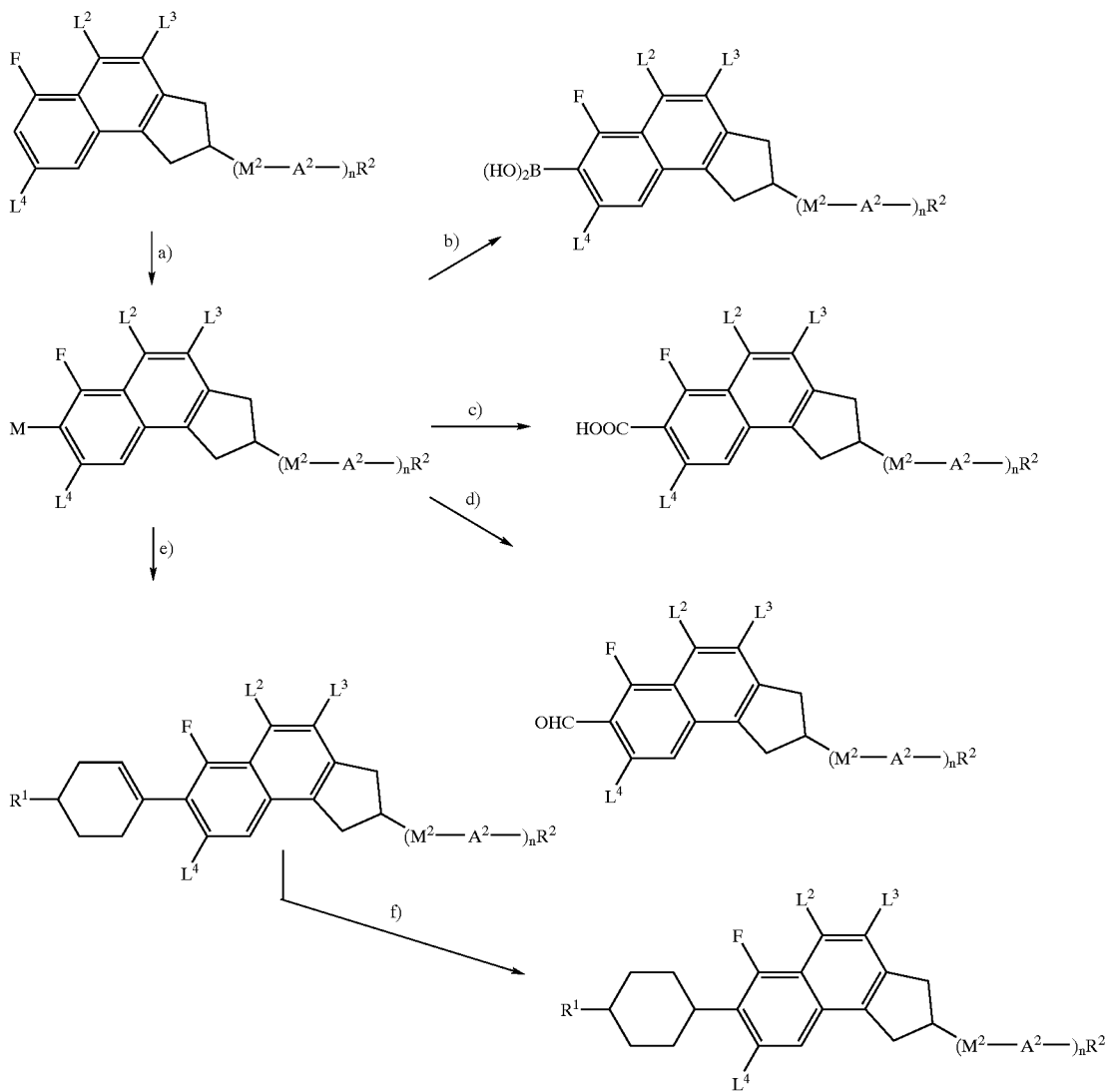
M = Li, K
a) n-BuLi/THF/hexane or n-BuLi/KOtBu/THF/hexane or sec-BuLi/THF/cyclohexane or LiTMP/THF/hexane
b) 1. B(OMe)$_3$ 2. H$_3$O$^+$
c) 1. CO$_2$ 2. H$_3$O$^+$
d) 1. DMF 2. H$_3$O$^+$
e) 1. 4-alkylcyclohexanone 2. H$_3$O$^+$ 3.cat. H$_2$SO$_4$/toluene
f) 4. H$_2$/ Pd—C /toluene
Scheme 6
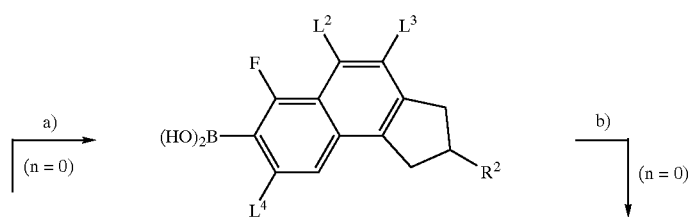

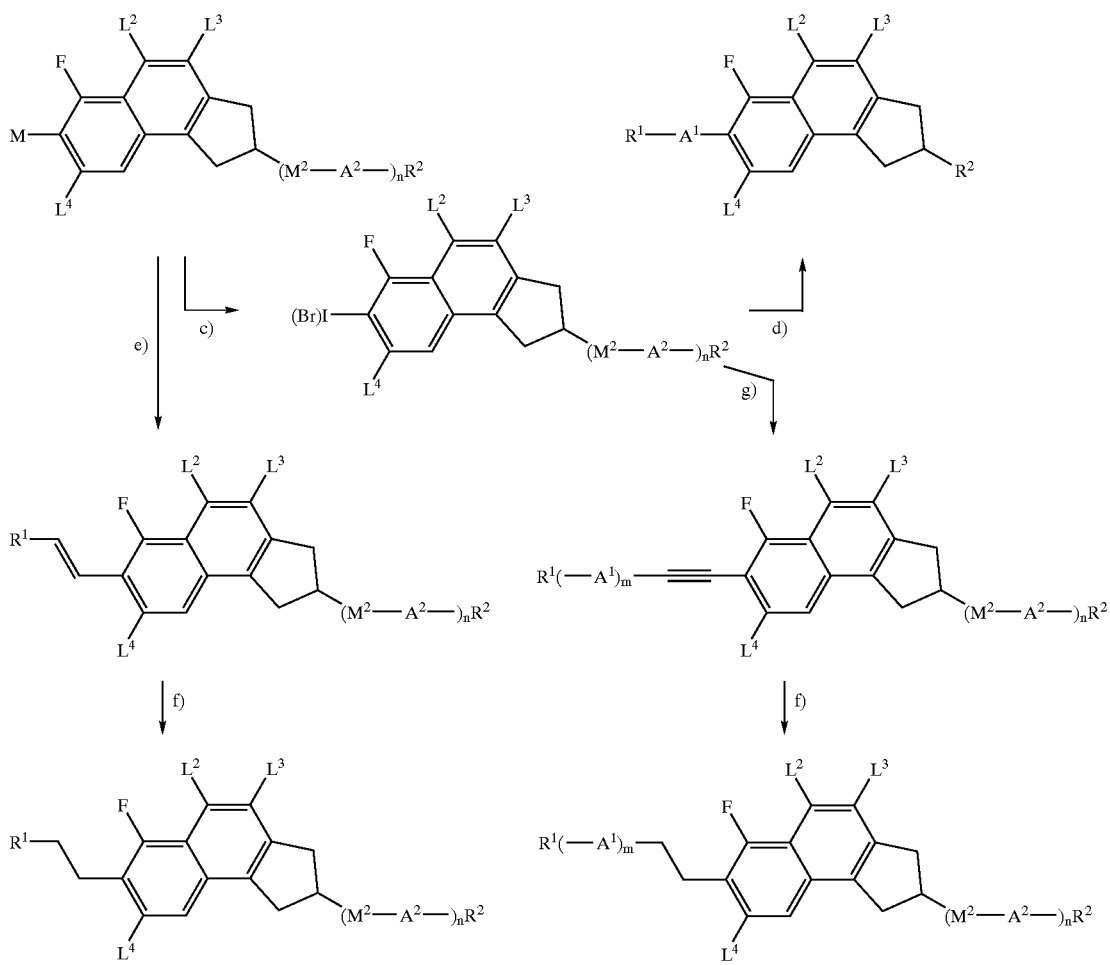
M = Li, K
a) 1. B(OMe)₃ 2. H₃O⁺
b) R¹—A¹—Hal/ Pd(PPh₃)₄/Na₂CO₃/toluene/EtOH/H₂O
c) I₂ (or Br₂)
d) R¹—A¹—B(OH)₂/ Pd(PPh₃)₄/Na₂CO₃/toluene/EtOH/H₂O
e) 1. R¹—CH₂CHO 2. H₃O⁺ 3. 4-TsOH/toluene
f) H₂/ Pd—C /THF
g) R¹—(A¹)ₘ—C≡CH /Pd(PPh₃)₂Cl₂/CuI/NEt₃
Scheme 7
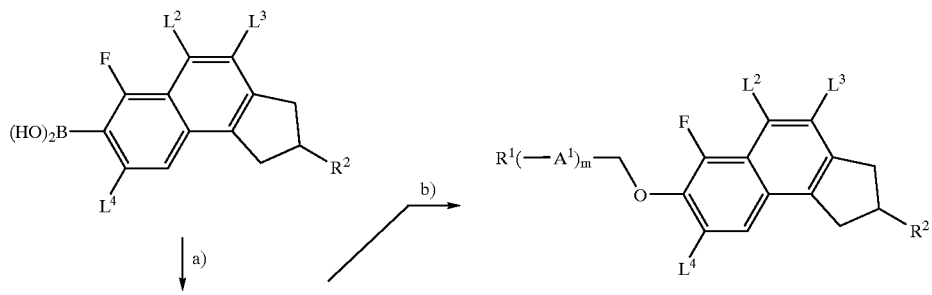

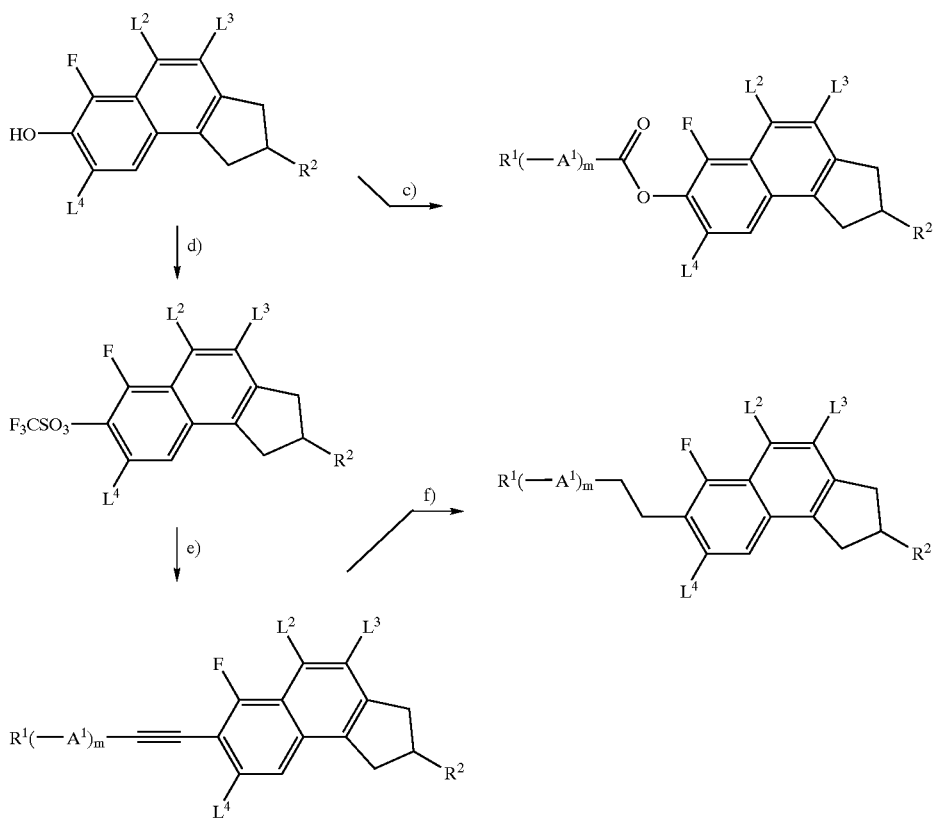
a) H₂O₂/MTBE
b) R¹(—A¹)ₘ—CH₂OH/DEAD/PPh₃/THF or R¹(—A¹)ₘ—CH₂Br /K₂CO₃/MEK
c) R¹(—A¹)ₘ—COOH/DCC/DMAP/CH₂Cl₂
d) (F₃CSO₂)₂O/pyridine
e) R¹(—A¹)ₘ—C≡CH/Pd(PPh₃)₂Cl₂/CuI/NEt₃
f) H₂/ Pd—C /THF
Scheme 8
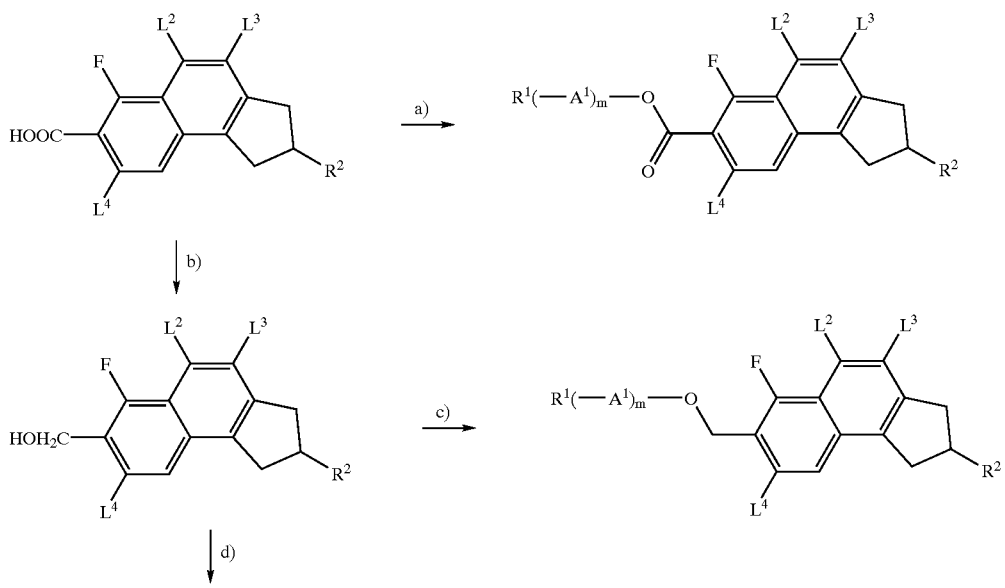

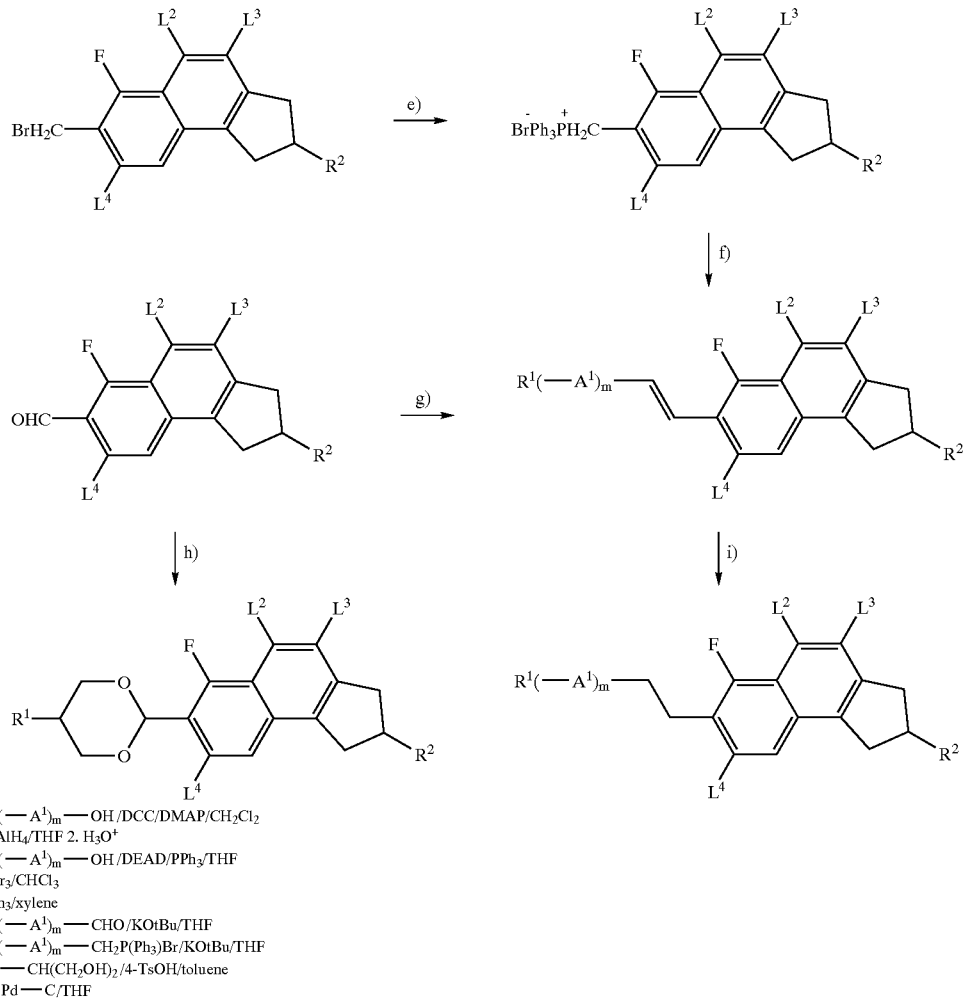

a) $R^1(-A^1)_m-OH/DCC/DMAP/CH_2Cl_2$
b) $LiAlH_4/THF$ 2. $H_3O^+$
c) $R^1(-A^1)_m-OH/DEAD/PPh_3/THF$
d) $PBr_3/CHCl_3$
e) $PPh_3$/xylene
f) $R^1(-A^1)_m-CHO/KOtBu/THF$
g) $R^1(-A^1)_m-CH_2P(Ph_3)Br/KOtBu/THF$
h) $R^1-CH(CH_2OH)_2$/4-TsOH/toluene
i) $H_2/Pd-C/THF$ By way of example, 7-methoxy-substituted cyclopenta[a] naphthalenes obtained in accordance with scheme 1 (X=H$_3$CO) may also be reacted in accordance with scheme 9 to give the compounds of the formula (I) according to the invention.

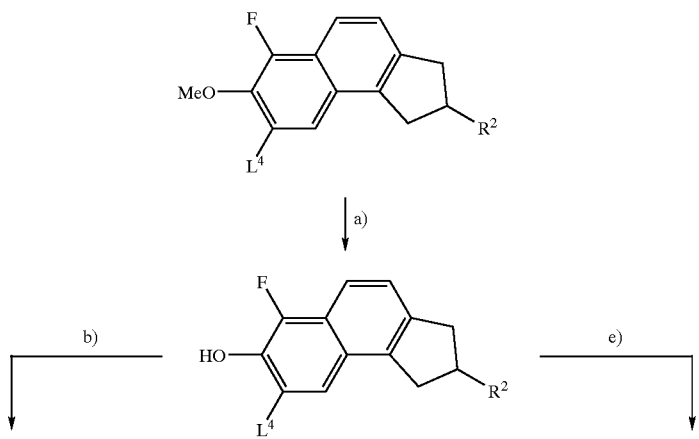

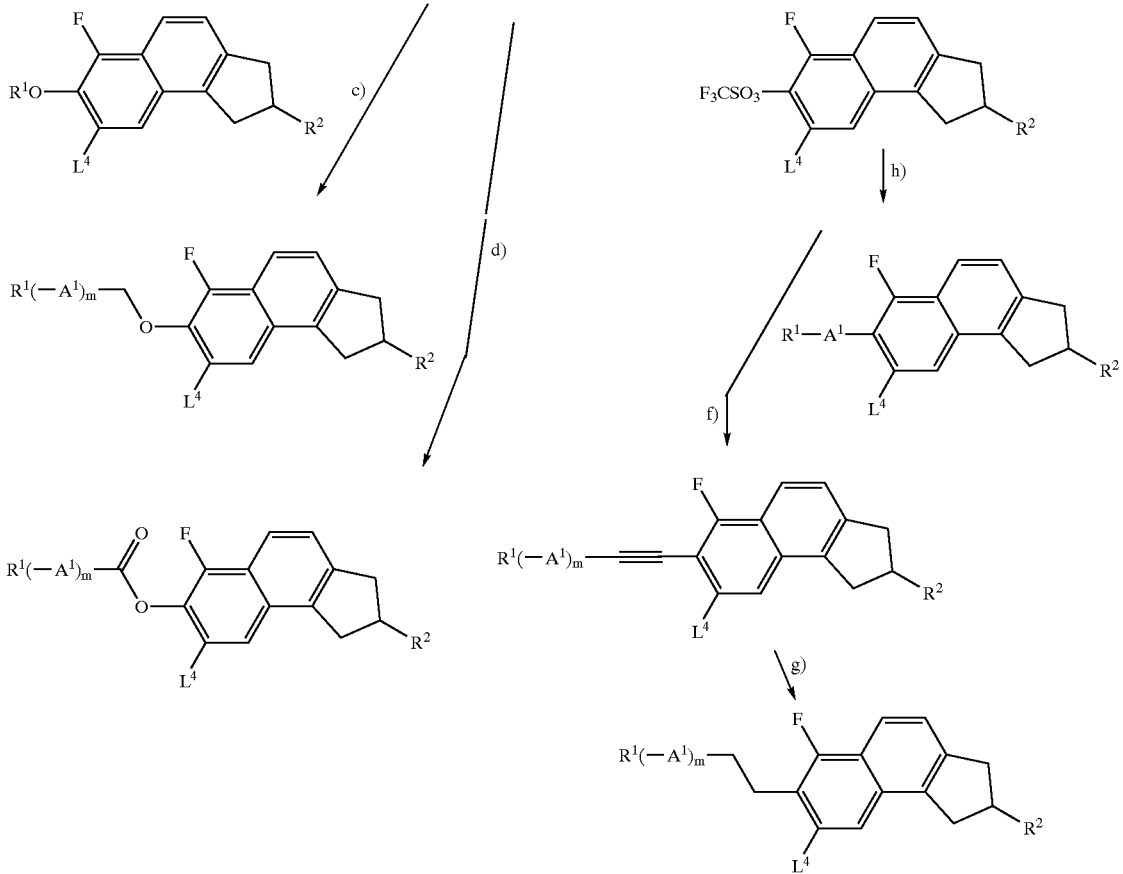

a) HBr/CH$_3$COOH or 1. BBr$_3$/CH$_2$Cl$_2$ 2. H$_3$O$^+$
b) R$^1$Br/K$_2$CO$_3$/MEK
c) R$^1$(—A$^1$)$_m$—COOH /DCC/DMAP/CH$_2$Cl$_2$
d) R$^1$(—A$^1$)$_m$—CH$_2$OH /DEAD/PPh$_3$/THF
e) (F$_3$CSO$_2$)$_2$O/pyridine
f) R$^1$(—A$^1$)$_m$—C≡CH/Pd(PPh$_3$)$_2$Cl$_2$/CuI/NEt$_3$
g) H$_2$/Pd—C/THF
h) R$^1$—A$^1$—B(OH)$_2$/Pd(PPh$_3$)$_4$/Na$_2$CO$_3$/toluene/EtOH/H$_2$O The preparation of the compounds required for the syntheses according to schemes 5 to 9, examples being alkyl-, alkenyl- or alkoxy-substituted, optionally additionally fluorinated benzoic acids, cyclohexanecarboxylic acids (schemes 7 and 9) phenylacetylenes (schemes 6, 7 and 9), phenylboronic acids (schemes 6 and 9), bromobenzenes (scheme 6), 2-alkylpropane-1,3-diols (scheme 8), and 4-alkylcyclohexanones (scheme 5) and their reactions are known to the skilled worker and are described, for example, in WO 96/00710, WO 96/30344, Liq. Cryst. 1995, 18, 1, Mol. Cryst. Liq. Cryst. 1991, 204, 43, Liq. Cryst. 1997, 23, 389, Synthesis 1996, 589, WO 92/11241, EP-A 0665825, J. Mater. Chem. 1999, 9, 1669 and Chem. Ber. 1985, 118, 3332. Appropriately substituted benzyl alcohols and (hydroxymethyl)cyclohexanes are R$^2$—A$^2$—CH$_2$OH (schemes 7, 9) can be obtained, for example, from the corresponding benzoic or cyclohexanecarboxylic acids R$^2$—A$^2$—COOH by reduction with lithium aluminum hydride (general procedure: Organikum, VEB Deutscher Verlag der Wissenschaften, 15th ed., Berlin 1984, section 7.3.4). Their bromination with phosphorus tribromide (in analogy to J. Org. Chem. 1984, 49, 2534–2540) provides the benzyl bromides and/or (bromomethyl)-cyclohexanes R$^2$—A$^2$—CH$_2$Br required in scheme 7. Subsequent reaction with triphenylphosphine in xylene gives the triphenylphosphonium bromides R$^2$—A$^2$—CH$_2$—P(Ph$_3$)Br which are mentioned in scheme 8. Correspondingly substituted benzaldehydes and cyclohexanecarboxaldehydes R$^2$—A$^2$—CHO (scheme 8) are available, for example, by reducing the respective carboxylic ester R$^2$—A$^2$—COOR (Bull. Korean Chem. Soc. 1999, 20, 1373) or oxidizing of the aforementioned benzyl alcohols and (hydroxymethyl)cyclohexanes R$^2$—A$^2$—CH$_2$OH (Tetrahedron Lett. 1968, 30, 3363).

Starting from the 7-hydroxy-substituted cyclopenta[a] naphthalenes (schemes 7 and 9) it is also possible, for example, to prepare the corresponding 7-trifluoromethoxy-substituted compounds of the formulae (Ih) and (II) (Bull. Chem. Soc. Jpn. 2000, 73, 471).

The synthesis of specific radicals X or Y takes place, for example, in accordance with DE-A 19528085, DE-A 19532292 and DE-A 19654487. Inventive compounds of the formula (I) with a 1-cyclohexene-1,4-diyl or 2-fluoro-1-cyclohexene-1,4-diyl- or 4-fluoro-3-cyclohexen-1-yl unit are prepared as described in Liq. Cryst. 1997, 23, 69, DE-A 4427266, DE-A 19607996, DE-A 19528665 and EP-A 0736513. As far as the synthesis of specific radicals R$^1$ and R$^2$ is concerned, reference may also be made, for example, to U.S. Pat. No. 4,798,680 (for optically active compounds with a 2-fluoroalkyloxy unit) and EP-A 0 318 423 (for compounds containing cyclopropyl groups in the side chain).

The compounds of the formula (I) are used preferably in nematic or cholesteric liquid-crystal mixtures. The liquid-crystal mixtures of the invention comprise at least one compound of the formula (I), preferably in an amount from 1 to 40% by weight, based on the liquid-crystal mixture. They preferably comprise at least 3 further components, selected from the known compounds having smectic and/or nematic and/or cholesteric phases. The selection of these further compounds (e.g., from the types listed in DE-A-19629812, pages 12 to 16) and the preparation of the liquid-crystal mixtures are familiar to the skilled worker.

The invention further provides a liquid-crystal display comprising these liquid-crystal mixtures. This liquid-crystal display preferably operates in IPS display mode (Kiefer et al., Japan Display '92, p. 547) or in VA display mode (Ohmura et al., SID 97 Digest, p. 845) or in ECB display mode (EP-A-0 474 062).

Preference is likewise given to using the compounds of the formula (I) in chiral smectic liquid-crystal mixtures. The liquid-crystal mixtures of the invention comprise at least one compound of the formula (I), preferably in an amount of from 1 to 40% by weight, based on the liquid-crystal mixture. They preferably comprise at least 3 further components. These components may be selected, for example, from the known compounds having smectic and/or nematic and/or cholesteric phases. The selection of these further compounds (e.g., from the types listed in DE-A-19857352) and also the preparation of the liquid-crystal mixtures are familiar to the skilled worker.

The invention also provides a liquid-crystal display comprising these liquid-crystal mixtures.

The invention is illustrated by the examples below.

EXAMPLE 1

A chiral smectic liquid-crystal mixture M1 (consisting of a plurality of derivatives of phenylpyrimidine and 2,3-difluorophenylpyrimidine) with a melting point of 7° C. is admixed with 15% of the compound 8,9-difluoro-7-(4-pentylphenyl)-2-propyl-2,3-dihydro-1H-cyclopenta[a]naphthalene [(Ia) where $R^1$=pentyl, $A^1$=phenylene-1,4-diyl, $M^1$=single bond, m=1, $R^2$=propyl; obtained starting from 4-bromo-2,3-difluoro-4'-pentyl-1,1'-biphenyl (prepared in analogy to Booth et al., J.Mater.Chem. 3, 395 (1993)) by way of the reaction sequence of Scheme 2]. The resulting mixture has a melting point of −3° C. The voltage/response time curve (FIG. 1) has the minimum required for inverse mode operation (e.g., "Fast High Contrast Ferroelectric Liquid Crystal Displays and the Role of Dielectric Biaxiality" by J. C. Jones, M. J. Towler, J. R. Hughes, Displays, Volume 14, No. 2(1993) 86–93 or M. Koden, Ferroelectrics 179, 121(1996)); the values achieved are within the industrially relevant range and the mixture is suitable for practical use.

EXAMPLE 2

A nematic liquid-crystal mixture M2 consisting of 50% by weight of 1-(3,4-difluorophenyl)-4-(4-vinyl)cyclohexylcyclohexane and 50% by weight of 1-[4-(3-butenyl)cyclohexyl]-4-(3,4-difluorophenyl)cyclohexane is admixed with 20% by weight of the compound 2-pentyl-6,7,8-trifluoro-2,3-dihydro-1H-cyclopenta[a]naphthalene [(Id) where $R^2$=pentyl; obtained starting from 3,4,5-trifluorobromobenzene by way of the reaction sequence of Scheme 1]; as a result of the addition of the compound of the invention, the dielectric anisotropy Δε has risen from 4.8 to 5.5.

What is claimed is:

1. A compound of the formula (I)

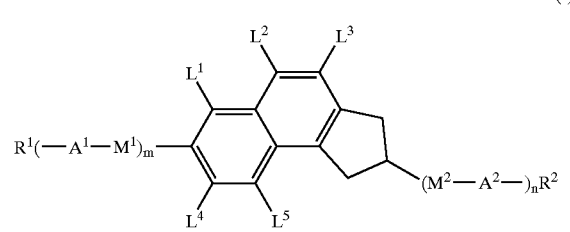

(I)

in which $R^1$ is H, F, $CF_3$, $OCF_3$, $OCF_2H$, $OCFH_2$, an alkyl radical or alkyloxy radical having from 1 to 12 carbon atoms or an alkenyl radical or alkenyloxy radical having from 2 to 12 carbon atoms, in which also in each case one (nonterminal) —$CH_2$— group may have been replaced by —O— or —C(=O)O—, one —$CH_2$— group may have been replaced by —C≡C— or cyclopropane-1,2-diyl and/or one or more H may have been replaced by F $R^2$ is H, an alkyl radical or alkyloxy radical having from 1 to 12 carbon atoms or an alkenyl radical or alkenyloxy radical having from 2 to 12 carbon atoms, in which also in each case one (nonterminal) —$CH_2$— group may have been replaced by —O— or —C(=O)O—, one —$CH_2$— group may have been replaced by —C≡C— or cyclopropane-1,2-diyl and/or one or more H may have been replaced by F with the proviso that $R^2$ may not be H if $R^1$ is H, F, $CF_3$, $OCF_3$, $OCF_2H$ or $OCFH_2$ $M^1$ is —C(=O)O—, —OC(=O)—, —$CH_2$O—, —$OCH_2$—, —$OCF_2$—, —$CF_2$O—, —C≡C—, —$CH_2CH_2$—, —$CF_2CF_2$—, —CF=CFC(=O)O— or a single bond $M^2$ is —C(=O)O—, —OC(=O)—, —$CH_2$O—, —$OCH_2$—, —$CH_2CH_2$—, —$CF_2CF_2$— or a single bond $A^1$ and $A^2$ independently of one another are phenylene-1,4-diyl, unsubstituted or mono- or disubstituted by F; cyclohexane-1,4-diyl, unsubstituted or mono- or disubstituted by F; 1-cyclohexene-1,4-diyl, unsubstituted or monosubstituted by F; or 1,3-dioxane-2,5-diyl m and n independently of one another are zero or 1; m+n=0 or 1

$L^1$, $L^2$, $L^3$, $L^4$ and $L^5$ are H or F with the provisos that
  a) at least one element from the group $L^1$, $L^2$, $L^3$, $L^4$, $L^5$ is F
  b) $L^1$, $L^2$ and $L^3$ are H if $L^5$ is F
  c) $L^4$ and $L^5$ are H if $L^3$ is F.

2. A compound of the formula (1) as claimed in claim 1, corresponding to one of the formulae (Ia) to (Ik)

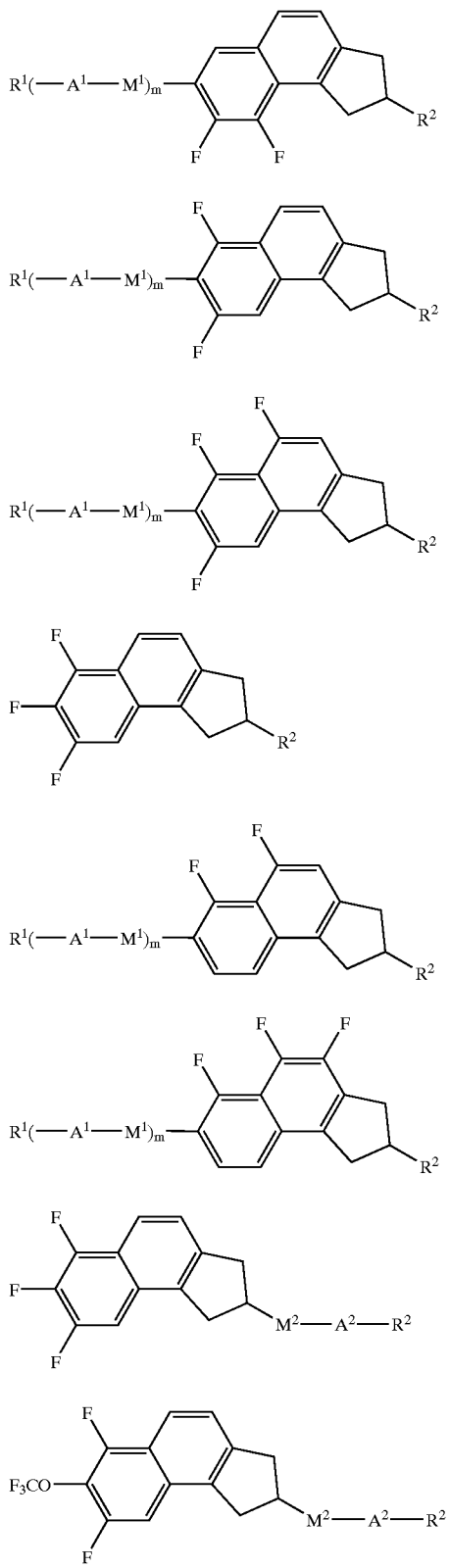

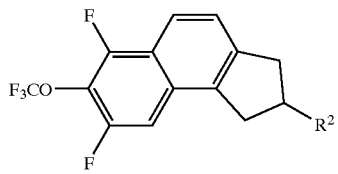

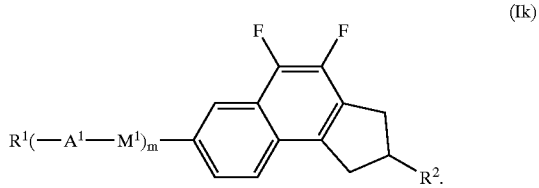

3. A liquid-crystal mixture, which comprises one or more compounds as claimed in claim 1.

4. A liquid-crystal mixture, which comprises one or more compounds as claimed in claim 2.

5. The liquid-crystal mixture as claimed in claim 3, which comprises one or more compounds of the formula (I) in an amount of from 1 to 40% by weight, based on the liquid-crystal mixture.

6. The liquid-crystal mixture as claimed in claim 3, which comprises at least three further components of smectic and/or nematic and/or cholesteric phases.

7. The liquid-crystal mixture as claimed in claim 3, which is chiral smectic.

8. The liquid-crystal mixture as claimed in claim 3, which is nematic or cholesteric.

9. A liquid-crystal display comprising a liquid-crystal mixture as claimed in claim 3.

10. The liquid-crystal display, which is operated in ECB, IPS or VA display mode and comprises a liquid-crystal mixture as claimed in claim 8.

11. The liquid-crystal mixture as claimed in claim 4, which comprises one or more compounds of the formula (I) in an amount of from 1 to 40% by weight, based on the liquid-crystal mixture.

12. The liquid-crystal mixture as claimed in claim 4, which comprises at least three further components of smectic and/or nematic and/or cholesteric phases.

13. The liquid-crystal mixture as claimed in claim 4, which is chiral smectic.

14. The liquid-crystal mixture as claimed in claim 4, which is nematic or cholesteric.

15. A liquid-crystal display comprising a liquid-crystal mixture as claimed in claim 4.

16. The liquid-crystal display, which is operated in ECB, IPS or VA display mode and comprises a liquid-crystal mixture as claimed in claim 14.

* * * * *